United States Patent
Alberico et al.

(10) Patent No.: US 6,232,302 B1
(45) Date of Patent: May 15, 2001

(54) AGENTS AND COMPOSITIONS THEREOF FOR THE HAIR TREATMENT

(75) Inventors: Pia Alberico, Como; Armando Cedro, Cislago; Danilo Moltrasio, Rovellasca; Roberto Porta, Cernobbio, all of (IT)

(73) Assignee: Crinos Industria Farmacobiologica S.p.A., Villa Guardia, Como (IT)

( * ) Notice: Subject to any disclaimer, the term of this patent is extended or adjusted under 35 U.S.C. 154(b) by 0 days.

(21) Appl. No.: 09/332,121

(22) Filed: Jun. 16, 1999

(30) Foreign Application Priority Data

Jun. 16, 1998 (IT) .............................. MI98A1367

(51) Int. Cl.$^7$ .......................... A61K 31/715; A61K 7/09; A61K 7/06
(52) U.S. Cl. ................... 514/54; 514/56; 514/59; 514/880; 514/881; 424/195.1; 424/520; 424/709; 424/70.1; 424/70.5
(58) Field of Search ................. 514/54, 880, 881, 514/56, 59; 424/195.1, 520, 709, 70.1, 70.5

(56) References Cited

U.S. PATENT DOCUMENTS 5,541,166 * 7/1996 Parish et al. ........................ 514/56

FOREIGN PATENT DOCUMENTS 0 730 867 A2   9/1996  (EP).
0 849 280 A2   6/1998  (EP).
965323       * 12/1999  (EP).

OTHER PUBLICATIONS

C. Orfanos, et al., "Human and Hair Diseases", misc. pages.
M.P. Philpott, et al. "Human Hair Growth inVitro", *Journal of Cell Science 97*, pp. 463–471 (1990).
G. E. Westgate, et al., "Prolonged Maintenance of Human Hair Follicles In Vitro in a Serum–Free Medium", *British Journal of Dermatology*, vol. 129, pp. 372–379 (1993).
C.S. Harmon et al., "Biphasic Effect of 1,25–Dihydroxyvitamin $D_3$ on Human Hair Follicle Growth and Hair Fiber Production in Whole–Organ Cultures", *The Journal of Investigative Dermatology*, vol. 103, No. 3, Sep. 1994.
M. Taylor, et al., "Cyclosporiin A Prolongs Human Hair Growth in Vitro", *The Journal of Investigative Dermatology*, vol. 100, No. 3, Mar. 1993.

* cited by examiner

Primary Examiner—Christopher R. Tate
(74) Attorney, Agent, or Firm—Arent Fox Kintner Plotkin & Kahn PLLC

(57) ABSTRACT

Compositions containing depolymerized fucane sulphates characterized by the following parameters (percentages by weight on the dry product):

Molecular weight: 5,000–30,000 dalton;
Sulphur: 5–16%;
Fucose: 25–60%;
Uronic acids 2–25%;

they increase the percentage of growing hair and inhibit the Pytirosporun growth on the skin.

7 Claims, No Drawings

AGENTS AND COMPOSITIONS THEREOF FOR THE HAIR TREATMENT

The present invention relates to products to be used as trichogen agents to be topically applied on the scalp, to normalize the hair growth cycle, and as antimycotic agents of the skin microflora, therefore able to reduce dandruff.

More specifically it relates to trichogen agents or compositions thereof having an improved efficacy in increasing the hair percentage in the growing phase, and at the same time active as skin antimicrobic agents, lacking of side effects of the prior art antimycotics and having high skin tolerability.

The hair growth cycle is subdivided in three subsequent phases which periodically repeat themselves during ones lifetime: the anagen phase, in which the hair stalk elongation takes place, the catagen phase, wherein the progressive keratinization of the hair bulb takes place and there is no stalk growth, and telogen phase, wherein there is no change of the hair bulb or of the hair stalk.

The anagen phase usually lasts many months or years, and is much longer than both the catagen phase (3 weeks) and the telogen one (3 months). Under normal conditions about 85% of hair is in anagen phase, 1% in catagen phase and 14% in telogen phase (C. E. Orfanos, R. H. Happle "Hair and hair disease" Springer-Verlag 1990). In subjects having androgenic alopecia both the anagen phase and the percentage of the growing hair is reduced.

A trichogen agent is defined according to the present invention as a substance able to increase the hair growing percentage. Therefore a trichogen agent can contribute to normalize the growth cycle, lengthening again the anagen phase. The substances used as trichogen agents must remain in contact with the skin for rather long periods and therefore they must not cause skin tolerability problems.

On the cutaneous surface and on the scalp a microflora is present among the main components of which lipophilic yeasts of Pytirosporum type, which grow in zones rich of lipids, are counted. The oval Pytirosporum is the most diffused yeast on the scalp.

The excessive growth of the oval Pytirosporum causes the dandruff appearance. In some people with increased sebaceous secretion the proliferation of this fungus can cause also the seborrheic dermatitis, charaterized by seborrhea, exfoliation and inflammation.

From the foregoing it is clear that in order to preserve the morphologic and functional integrity of the skin and of the scalp it is important to maintain the host microflora at physiologic levels.

In order to reach this aim, according to the prior art, the skin is treated with preparations containing compounds having antimycotic activity as ketoconazole, lithium succinate, zinc pirythione, selenium sulphide. These compounds can cause undesired effects on the skin and on the scalp. For example ketoconazole causes local inflammation, dermatites; the lithium succinate is contra-indicated in patients affected by psoriasis since it is a disagreeable inflammatory agent, zinc pirythione can cause peripheral neurites and selenium sulphide can cause inflammation of the scalp, of the conjunctiva and of the internal part of the skin folds. Consequently the contact times with the skin of the preparations containing these compounds must be reduced.

From the foregoing it is clear that according to the prior art it is not possible to carry out a single treatment to normalize the hair growth cycle and to prevent or reduce the dandruff.

It is also known that compounds that are to be used for the percutaneous supply must have a low molecular weight in order to be easily absorbed through the skin. It is also known that to obtain the topic absorption of the natural polymers it is necessary to lower the molecular weight thereof, generally high and in the range of various hundreds of Kilodalton, by a depolymerization process.

The European patent application EP 730,867 relates to the use in the skin and hair dermatological and cosmetic treatment, and in the scalp alopecia, of polymers obtained by depolymerization of polyanions of vegetable origin. The depolymerized products have a molecular weight-range between 5,000 and 100,000, and sulphur content in the range 5–20% by weight. Examples showing the trichogen activity of these products are not supplied, neither are described nor reference is made to methods allowing to obtain these compounds. No mention is made to the fact that the compounds reported in said patent application are active agents in inhibiting the Pytirosporum growth. Tests carried out by the Applicant have shown that among the polymers having the specifications of the depolymerized fucans reported in the patent application EP 730,867, obtained according to the processes of the prior art (see the comparative example) no product able to inhibit the Pytirosporum growth and therefore having antidandruff activity, is obtained, and besides the growth activity is meaningless.

The need was felt to use compounds being effective agents in increasing the hair percentage in the growing phase and at the same time skin antimicrobic agents, specifically active in the dandruff reduction and without the side effects of the prior art antimycotics and having high cutaneous tolerability.

It has been unexpectedly and surprisingly found that it is possible to meet altogether said requirements by using a particular class of depolymerized fucane sulphates having specific characteristics, which result effective in increasing the percentage of hair in the growimg phase and which are able to inhibit the Pytirosporum growth, both on the skin and on the scalp and besides they are lacking of side effects.

An object of the present invention are depolymerized fucane sulphates and their use as trichogen agents characterized by the following parameters (the percentages are by weight on the dry product):

Weight average molecular weight: greater than 5,000–30,000 dalton, preferably 5,500–30,000 dalton Sulphur: 5–16%;

Fucose: 25–60%;

Uronic acids: 2–25%;

Specifically the fucanes as above defined are able to inhibit the oval Pytirosporum growth.

The depolymerized fucanes obtainable from *Fucus vesiculosus, Ascophyllum nodosum, Ecklonia kurome, Eisenia bicyclis, Laminaria digitata, Laminaria japonica, Padina pavonia, Pelvetia canaliculata, Sargassum linifolium, Undaria pinnatifda* are particularly preferred.

The methods for determining these parameters are described in the European published application No. 849,280 in the name of the Applicant, herein incorporated by reference.

The depolymerized fucane from brown algae having molecular weight 14,000–30,000 dalton to be used in the present invention are obtainable with the process described in the European published application No. 849,280 herein incorporated by reference.

The polymers having molecular weight lower than 14,000 dalton with the following chemical and chemical-phisical characteristics:

Weight average molecular weight: greater than 5,000–14,000 dalton

Sulphur: 5–12.5%

Fucose: 25–43%

Uronic acids: 9–25% are obtainable with the following process:

a) dispersion in water under stirring of the alga dry and milled powder, or of the vegetable material as such, in water, so as to have a dry concentration of 12.5% w/w, at a temperature in the range 92–100° C., extracting the vegetable material under these conditions for 16 hours;

b) suspension filtering and filtrate pH correction at a value in the range 2.0–2.5, removal of the precipitate formed by filtering, surnatant pH correction at a value in the range 6.5–7.5;

c) ultrafiltering on membrane having cut-off of 100,000 dalton to reduce the solution volume to ¼–⅕ of the initial one, subsequent dialysis in the same equipment against 3 volumes of distilled water, optionally followed by a concentration step;

d) solution salting, addition of two volumes of a precipitating solvent, preferably of ethanol or acetone, and recovery of the crude extract;

e) depolymerization at the temperature of 55° C. of the crude extract in aqueous solution in the presence of an inorganic salt Cu (II) in % weight ratio with the extract in the range 0.12–0.14%, and of 8% hydrogen peroxide in such amount that the ratio between the weight of the crude extract and the ml volume of the 8% hydrogen peroxide is in the range ¼–¹⁄₁₀, for the necessary time, determined by lab. tests, to reduce the molecular weight in the range greater than 5,000 and 14,000;

f) solution filtering, salting and precipitation of the depolymerized fucanes Cu (II) salts by addition of 2–3 volumes of a precipitating solvent, preferably of ethanol or acetone;

g) precipitate dissolution in water at a concentration between 5 and 7% w/v and treatment with an ionic exchange resin in the $Na^+$ form for about ten hours under slow stirring; resin removal and pH correction at a value in the range 6.0–7.0; salting and precipitation of the depolymerized fucanes in the form of their corresponding sodic salts by addition of 2–3 volumes of a precipitating solvent, preferably ethanol or acetone.

The experimental model which has been used in the present patent application to show that the invention depolymerized fucanes have an improved efficacy in increasing the percentage of the growing hair is described in the publication by M. P. Philpott et al. "Human hair growth in vitro" J. Cell. Sci. 1990, 97 463–471, modified by G. E. Westgate "Prolonged maintenance of human hair follicles in vitro in a serum free medium" J. Cell. Sci. 1993, 129 372–379. The Applicant has used in this experiment sound piliferous follicles, separated by strips of human scalp taken from the occipital zone of male subjects during autografting operations. The piliferous follicles have been cultured in suitable culture medium, containing the substances under examination, as specififed in the Examples.

This model reproduces the following main aspects of the normal physiological cycle of the piliferous follicle:

1) The growth rate of the hair stalk or stem (C. S. Harmon et alii, J. Invest. Dermatol. 1994, 103, 318–322).

2) the same anagen/catagen transition: the stalk proximal keratinization and the dermatic papilla condensation at the end of the anagen phase, which are the same morphological changes observed in vivo in the passage from the anagen phase to the catagen one (M. Taylor et alii, J. Invest. Dermatol. 1993, 100 237–239).

3) The inhibition by means of testosterone or of the epidermal growth factor (C. S. Harmon, see above) of the growth of the follicles in culture, with decrease of the amount of growing follicles.

In the prior art it has been verified that the cyclosporine A (M. Taylor, see above), which causes the side effect of the hairs growth in men, in the same model used by the Applicant, has prolonged the period of hair growth of human piliferous follicles. Therefore the model used in the present invention is predictive of the in vivo activity.

The depolymerized fucanes with the above described chemical and chemical-physical characteristics have shown themselves active in increasing in a statistically meaningful way (w<0.01) the percentage of the growing follicles, with rspect to the untreated controls, for the whole duration of the experiment (28 days) at the used concentration.

These compounds are therefore effective agents for topic administration on the scalp, to normalize the duration of the anagen phase in the cases in which it is reduced such as for example in alopecia.

Surprisingly the invention depolymerized compounds have shown themselves effective agents in inhibiting the oval Pytirosporum growth at very low concentrations, lower than 0.1% w/v.

Therefore the use of the invention depolymerized fucans as antimycotic agents is possible.

The acid depolymerization product of the comparative example has on the contrary no antimycotic property on the oval Pytirosporum.

The tolerability of the preparations containing the fucan sulphates of the invention has resulted very good.

The fucans according to the present invention, topically applied in cosmetic formulations prepared according to the prior art, result effective also in maintaining the cutaneous hydration physiological levels. Consequently the topic application on the skin of these susbstances allows to obtain various advantages.

The uses foreseen in the present invention are achieved by using fucane sulphates carried in preparations for topic use at concentrations in the range 0.01–20%. For compositions under the form of lotions and shampoos, that preferably are to be used for the scalp, concentrations of fucane sulphate in the range 0.01–1% are preferably used. In the creams and gel formulations, concentrations from 1 to 20% w/v are preferably used.

The preparations containing the depolymerized fucane sulphates of the present invention are topically applied, locally on the skin or on the scalp, by rubbing to facilitate the absorption thereof or optionally by devices known in the prior art (e.g. patch).

The preparations containing the depolymerized fucane sulphates of the present invetion are prepared according to methods well known to the skilled in the art. See for example in Remington's Pharmaceutical Sciences 15a Ed.

The following examples are given with the only purpose to illustrate the invention without limiting it.

EXAMPLE 1

Extraction of the Crude Fucane Sulphate, Preparation No. V0246.B

In a 300 liter reactor 175 liters of distilled water are poured. 25 kg of Fucus vesiculosus dry powder are added and heated with vapour jacket at 92° C. for 16 hours. At the end the content is cooled at 30° C., 5 kg of Clarcel FLO/MA® are added, then the content is filtered on filter press using Seitz K 800® filters, collecting the filtrate and dispersing the solid layer in water (20 liters) keeping under stirring for 1 h at 60° C. It is filtered on Seitz K 800® filters, the liquids are joined together (220 liters) and are poured in a reactor equipped with cooling jacket. 5.5 kg of Clarcel CBR® (calcined and milled diatom powder) are added. Maintaining the temperature inside the reactor between 25 and 30° C., 1.5 liters about of 37% HCl are added under stirring. The solution pH lowers to 2. Stirring is continued for 15 minutes after the acid addition and the content is filtered on Seitz K 800® filters. The solid layers are dispersed in 20 liters of hydrochloric acid diluted at pH 2 and filtered again. The liquid phases are joined together. The solution is fed to an Alfa Laval® ultrafiltration plant equipped with a Millipore® ultrafiltration cartridge having cut-off=100,000. The solution is concentrated so as to reduce the volume to 50 liters, then it is dialyzed at constant volume against 3 volumes of distilled water. When the dialysis is over, the volume of the solution is further reduced to 25–30 liters. The liquid is discharged, salted by adding NaCl up to a salt concentration 2% w/v and the crude extract is precipitated by adding 2 acetone volumes. After decantation the solid is recovered and dehydrated, dried and milled. The obtained crude extract V0246.B weighs 1665 g (yield 6.7%). The analytical data on the dry product are the following: sulphur: 7.1%, fucose 32.0%, uronic acids 25.0%, molecular weight 800,000.

EXAMPLE 2
Extraction of the Crude Fucane Sulphate, Preparation V0246.C

The preceding Example is repeated by starting from 25 kg of a new lot of Fucus vesiculosus. The intermediate precipitation pH is of 2.5. 2100 g (yield 8.4%) of product n. batch V0246.C are obtained. Analytical determinations: sulphur 7.6%, fucosium 35.8%, uronic acids 26.1%, molecular weight 470,000.

EXAMPLE 3
Extraction of the Crude Fucane Sulphate, Preparation V0246.D

The Example 1 is repeated starting from 25 kg of a new lot of Fucus vesiculosus. 2470 g (yield 9.9%) of product VO246.D are obtained. Analytical determinations: sulphur 6.2%, fucose 36.3%, uronic acids 22.1%, molecular weight 1,007,000.

EXAMPLE 4
Depolymerization of the Crude Material V0246.C with Copper Salts and Obtainment of the Depolymerized Fucane Sulphate Prep. No. 0195/97086-A 20 g of V0246.C are dissolved in 400 ml of distilled water (5% w/v concentration). The solution is heated to 55° C. and 80 mg of monohydrated cupric acetate are added, correcting the pH to 7.5 with a NaOH 1 N solution. With a peristaltic pump, regulated at a 18.5 ml/h flow, a 8% w/v hydrogen peroxide solution is added, maintaining the solution pH at the 6 value gradually adding a 30% NaOH solution. On the basis of the molecular weight determinations, after 6 hours the depolymerization is stopped (total volume of hydrogen peroxide employed: 110 ml). The content is cooled at room temperature, salted with sodium acetate until having a 7% w/v salt concentration and three volumes of ethanol are added. It is dehydrated and dried. The precipitate (9.1 g) is redissolved in 140 ml of deionized water and 95 ml of ionic exchange resin Amberlite IRC 718® (form $Na^+$) are added. It is left under slow stirring for one night. The solution is recovered, the resin is washed with two volumes of distilled water and filtered on buckner with Clarcel CBR® layer having the same weight as that of the powder recovered after the depolymerization. The limpid solution is salted with anhydrous sodium acetate until having a 7% w/v concentration. The solution is precipitated with 3 ethanol volumes. After dehydration and drying 7.1 g of depolymerized fucane sulphate prep. No. 0195/97086-A are obtained. Analytical determinations: sulphur: 8.6%, fucose 30.0%, uronic acids 16.1%, molecular weight 5,600.

EXAMPLE 5
Depolymerization of the Crude Material V0246.C with Copper Salts and Obtainment of the Depolymerized Fucane Sulphate, Prep. No. V0268.B 300 g of V0246.C are dissolved in 6 liters of distilled water. The solution is heated is heated to 55° C. and 1.2 g of monohydrated cupric acetate are added, correcting the pH at 7.5 with a NaOH 1 N solution. With a peristaltic pump, regulated at a 18.3 ml/h flow, a 8% w/v hydrogen peroxide solution is added, maintaining the solution pH at the 6.5 value by gradually adding NaOH 30%. On the basis of the molecular weight determinations, after 1.5 hours the depolymerization is stopped (total volume of hydrogen peroxide used: 1.65 liters). One proceeds to recover the depolymerized product as described in Example 4. It is dehydrated and dried. The precipitate (173 g) is redissolved in 2.6 liters of deionized water and 1.73 liters of ionic exchange resin Amberlite IRC 718® (form $Na^+$) are added, by keeping under slow stirring for one night. One proceeds as described in Example 4. After dehydration and drying, 139.5 g of the depolymerized fucane sulphate (yield 46%) prep. No. V0268.B are obtained. Analytical determinations: sulphur: 7.0%, fucose 28.5%, uronic acids 15.4%, molecular weight 10,700.

EXAMPLE 6
Depolymerization of the Crude Material V0246.B with Copper Salts and Obtainment of the Depolymerized Fucane Sulphate, Prep. No. V0264.B 100 g of V0246.B are dissolved in 2 liters of distilled water. The solution is heated to 55° C. and 4 g of monohydrated cupric acetate are added, correcting the pH at 7.5 with a NaOH 1 N solution. With a peristaltic pump, regulated at a 108.3 ml/h flow, a 8% w/v hydrogen peroxide solution is added, maintaining the solution pH at a value comprised between 6.0 and 6.5 by gradually adding NaOH 30%. On the basis of the molecular weight determinations, after 24 hours the depolymerization is stopped (total volume of hydrogen peroxide employed: 2,600 liters). One proceeds as described in Example 4. It is dehydrated and dried. The precipitate (23.2 g) is redissolved in 400 ml of deionized water and 260 ml of ionic exchange resin Amberlite IRC 718® (form $Na^+$) are added, by keeping under slow stirring for one night. One proceeds as described in Example 4. After dehydration and drying 16.4 g of the depolymerized fucane sulphate (yield 16.4%) prep. No. V0264.B are obtained. Analytical determinations: sulphur: 14.3%, fucose 44.2%, uronic acids 3.4%, molecular weight 17,500.

EXAMPLE 7
Depolymerization of the Crude Material V0246.C with Copper Salts and Obtainment of the Depolymerized Fucane Sulphate Prep. No. V0260.C 20 g of V0246.C are dissolved in 4 liters of distilled water. The solution is heated to 55° C. and 8 g of monohydrated cupric acetate are added, correcting the pH at 7.5 with a NaOH 1 N solution. With a peristaltic pump, regulated at a 183.3 ml/h flow, a 8% w/v hydrogen peroxide solution is added, maintaining the solution pH at a value comprised between 6.0 and 6.5 by gradually adding NaOH 30%. On the basis of the molecular weight determinations, after 6 hours the depolymerization is stopped (total volume of hydrogen peroxide: 1,100 liters). A trihydrated sodic acetate solution is added until a 11% w/v solution concentration is obtained and it is precipitated with two ethanol volumes. It is dehydrated and dried. The precipitate (79 g) is redissolved in 1.2 liters of deionized water. One centrifuges at 3000 rpm amd 800 ml of ionic exchange resin Amberlite IRC 718® (form $Na^+$) are added, by keeping under slow stirring for one night. One proceeds as in Example 4, filtering on buckner with 15 g of Clarcel CBR® layer. The pH is corrected at 6.5 and one proceeds as in Example 4, precipitating with two ethanol volumes. 60.1 g of the depolymerized fucane sulphate (yield 30.1%) prep. No. V0260.C are obtained. Analytical determinations: sulphur: 12.6%, fucose 47%, uronic acids 8.1%, molecular weight 29,000.

EXAMPLE 8
Depolymerization in Acid Ambient of the Crude Fucane Sulphate V0246.B 5 g of crude extract are dissolved in 500 ml of distilled water and 10 ml of HCl 1 are added. In this way the solution pH lowers to about 2.2, i.e. to a weakly acid value, such as to allow that the compound is mildly hydrolysed. The solution is heated to 60° C. for 12 hours. The solution is cooled and neutralized by adding few ml of NaOH 30% w/v. The liquid is dialyzed in Amicon® CH2-A ultrafiltration equipment at a constant volume, in consecutive passages, each time against 5 volumes of distilled water. In the first passage a membrane having cut-off of 3,000 Da is used, in the second one of 10,000 Da and in the third one of 100,000 Da. The permeate of the last dialysis is salted with NaCl up to a 2% w/v concentration and 2 acetone volumes are added. 0.5 g of the preparation 0195/95026-D having the following analytical characteristics: molecular weight 65,000, sulphur 5.2%, uronic acids 20.1%, fucose 21.2%, are obtained. This preparation has been used for the comparative biologic and microbiologic tests of Examples 11B and 12B.

EXAMPLE 9
Extraction of the Crude Fucane Sulphate Preparation V0271.A

1 Kg of Asophyllum nodosum dry powder are suspended under stirring in 7 liters of distilled water in a 15 l flask equipped with refrigerant. When the suspension has been carried out (about 15 minutes) it is heated in oil bath to 100° C. for 16 hours. It is cooled to 40° C., the suspension is centrifuged at 3,000 rev. per 20 minutes by using four 1 liter centrifuge test tubes. The gelatinous residue which accumulates on the bottom of the tubes is suspended in 3 liters of water at the temperature of 60° C., by mechanical stirring, maintaining the stirring for about 15 minutes. It is recentrifuged and the so obtained surnatant is joined to the previous one. To the joined together surnatants (7.5 liters) 20 g of Clarcel CBR® (calcined and milled perlite) are added. It is filtered on Seitz K 800® recovering 6.65 liters of filtrate; the pH is corrected at 2.0 by addition of 330 ml of HCl 2 N and it is centrifuged again. The surnatant is neutralized (pH 6.5) with about 70 ml of a NaOH 30% solution, then it is concentrated mantaining the volume constant at 1.5 liters in Amicon® CH2-A ultrafiltering equipment on which a membrane with cut-off of 100,000 Da has been set up. When the concentration phase is over, the solution is dialyzed by using the same membrane and three volumes of distilled water.

To the retentate 945 g (7% w/v) of anhydrous sodium acetate are added, it is stirred until an homogeneous solution is obtained and the solute is precipitated with two 95% ethanol volumes. It is allowed to decant for one night and the solid is dehydrated and dried. 75.46 g (yield 8.4%) of a solid (preparation V0271.A) having the following analytical data: sulphur 5.2%, fucose 25.2%, uronic acids 19.7%, molecular weight 483,000, are recovered.

EXAMPLE 10
Depolymerization of the Fucane Sulphate V0271.A with Copper Salts and Obtainment of the Depolymerized Fucane Sulphate, Prep. No. V0272.A 25 g of V0271.A are dissolved in 500 ml of distilled water (concentration 5% w/v). It is heated to 55° C. and 100 mg of monohydrated cupric acetate are added, correcting the pH at 7.5 with a NaOH 1 N solution. With a peristaltic pump, regulated at a 18.5 ml/h flow, a 8% w/v solution of hydrogen peroxide (total 137.5 ml) is added, maintaining the solution pH at a 6.50 value by gradually adding a NaOH 30% solution. On the basis of the molecular weight determinations, after 24 hours the depolymerization is stopped. It is cooled at room temperature, the surnatant is decanted, salted with sodium acetate until a 7% w/v salt concentration is obtained and two ethanol volumes are added. It is dehydrated and dried. The precipitate (9 g) is redissolved in 130 ml of deionized water and 90 ml of ionic exchange resin Amberlite IRC 718® (form Na$^+$) are added. It is left under slow stirring for one night. The solution is recovered, the resin is washed with two volumes of distilled water and filtered on buckner with Clarcel CBR® layer having the same weight as the one of the recovered powder after depolymerization. The limpid solution is salted with anhydrous sodium acetate until a 7% w/v concentration is obtained. It is precipitated with 2 ethanol volumes. After dehydration and drying 7.5 g of depolymerized fucane sulphate V0272.A are obtained. Analytical determinations: sulphur: 9.2%, fucose 32.7%, uronic acids 17.3%, molecular weight 8,900.

EXAMPLE 11

Examples 11A
Method to Evaluate the Efficacy of the Invention Fucane Sulphate Preparation V0268.B in Increasing the Growing Piliferous Follicle Percentage.

The piliferous follicles are taken from the occipital zone of male people, carefully cleaned up, and placed in cups containing 1 ml of nourishing medium William's medium E (ICN catalogue 1995). The medium is charged with 10 ng/ml of hydrocortisone, 10 µg/ml of insulin, 2 mmoles of glutamine and with an antimicrobic complex comprising streptomycin 100 µg/ml, penicillin 100 U/ml, amphothericin B 0.25 µg/ml. The cultures have been charged with an amount of depolymerized fucane sulphate such as to obtain a compound concentration of 80 µg/ml respectively. The follicles used in the experiment have been obtained from No. 10 different people (12 follicles taken from each people) and subdivided in 2 groups (control and the group treated at the above indicated fucan sulphate concentration) . Each group has been repeated 6 times. The cultures have been incubated at 37° C. at humidified atmosphere containing 5% $CO_2$, for 28 days. At the tenth and 21st day the culture medium has been replaced with a fresh amount of the same medium. The length of the hair stalk portion external to the follicle has been measured immediately after the isolation of each follicle, and then at the third, seventh, tenth, fourteenth, seventeenth, twentyfirst, twentyfourth and twentyeighth culture day. The criterium to determine how many follicles were in the growth phase was that the increase of the stalk length, calculated as the difference (1"–1') wherein 1"=present length, 1'=length determined on the day of the previous determination, had to be different from zero.

In the experiment the VO 268.B preparation has been used and the respective results are reported in Table I and it is noticed, in particular, that on the twentyfirst day from the treatment beginning, the percentage of the growing follicles is more than the double with respect to the untreated follicles.

Example 11B (comparative)
Activity Determination of the Example 8 Preparation Obtained by Acid Depolymerization By using the method described in Example 11A by employing the preparation obtained by acid depolymerization of Example 8 at the dose of 80 µg/ml, the results reported in Table II have been obtained. From the Table it results that at all times the percentage of the growing piliferous follicles in the medium charged with fucane sulphate having low molecular weight obtained by acid depolymerization gets near the one of the control group. Therefore this fucane sulphate is not very active in comparison with the fucane sulphates of the present invention.

Example 11C
Activity Determination of the Invention Preparations of Examples 4, 6, 7 and 10

The experiment of Example 11A has been repeated with the 195/97086-A (Ex. 4), V0264.B (Ex. 6), V0260.C (Ex. 7) and V0272.A (Ex. 10) preparation. Table III reports the percentage of growing piliferous follicles on the seventeenth day of observation in culture mediums charged with different preparations of fucane sulphate according to the present invention at the 80 μg/ml concentration. It is noticed that the percentage of growing piliferous follicles is meaningfully higher than the percentage of the control group follicles and the obtained values are comprised in a rather small range and they can be considered among them homogeneous.

EXAMPLE 12

Example 12A
Determination of the Antimicrobic Activity in Vitro of Fucan Sulphates V0268.B (inhibition in vitro of the growth of the oval Pytirosporum yeast) and of the Product Obtained by Acid Depolymerization According to Example 8

The used stock is the ATCC 12078 one, supplied by Istituto Sieroterapico of Milano—Italy. The stock has been suspended in 100 ml of physiological solution (mother solution, M).

1) Total Microbic Count in Liquid Medium.

Two 100 ml portions of a generic culture medium have been prepared, by dissolving in 1000 ml of distilled water, 5 g of NaCl and 10 g of peptone (nourishing medium); to each portion 10 ml of mother solution have been added.

In one of the two suspensions the powdered product to be examined has been added until a concentration of 1 mg/ml (sample B) has been obtained; the other suspension is sample A. After incubation at a temperature of 36° C. for 48 hours the total microbic count (TMC) has been determined by subsequent dilutions and spreading of 1 ml on the plate.

2) Total Microbic Count in Solid Medium.

At the same time of the previous count the TMC related to the mother solution has been determined using two different plates, one as reference (sample 1) and the other charged with the sample under examination (sample 2). The results obtained have been the following:

1) Total microbic count in solid medium:

Sample A (white): $1.9 \times 10^2$ units forming colonies (u.f.c.)/1 g of mother solution;

Sample B (with the compound under examination): <1 unit forming colonies/1 g of mother solution 2) Total microbic count in liquid medium:

Sample 1 (white): $8.2 \times 10^2$ units forming colonies/1 g of mother solution;

Sample 2 (with the compound under examination): <1 unit forming colonies/1 g of mother solution.

Example 12B (comparative)
Determination of the Antibacterial Activity in Vitro of the Product Obtained by Acid Depolymerization According to Example 8

According to the method of Example 12A, the antimicrobic activity of the compound obtained in Example 8 has been determined.

The results have been the following:

1) Total microbic count in solid medium:

Sample A (white): $>5 \times 10^7$ units forming colonies (u.f.c.)/1 g of mother solution;

Sample B (with the compound under examination): $>5 \times 10^7$ units forming colonies/1 g of mother solution 2) Total microbic count in liquid medium:

Sample 1 (white): $>5 \times 10^7$ units forming colonies/1 g of mother solution;

Sample 2 (with the compound under examination) $>5 \times 10^7$ units forming colonies/1 g of mother solution.

Therefore the compound has no antibacterial activity.

EXAMPLE 13
Formulations of the Depolymerized Fucan Sulphates in Hydroalcoholic Solution

| hair lotion | | A | B |
|---|---|---|---|
| fucane sulphates prep. VO268.B | g | 0.4 | 2 |
| ethyl alcohol | ml | 10 | 8 |
| propylene glycol | g | 4 | 4 |
| conservants, perfume, | g | 100 | 100 |
| water as it suffices to | | | |

EXAMPLE 14
Cutaneous Tolerability Tests of the V0268.B Preparation

The Example 13B formulation has been applied in the volar part of the forearm of No. 20 volunteers by occlusive patch test for 48 hours. After patch removal, the visual evaluations of the application zone have been carried out at the following intervals: 15 minutes, 24, 48 and 72 hours. At all times of the observation no meaningful cutaneous alterations have been noticed.

EXAMPLE 15

| Formulation of the depolymerized fucane sulphates in cream | |
|---|---|
| depolym. fucane sulphates | g 3.00 |
| gelling agent (carbomer) | g 0.20 |
| glycerine | g 5.00 |
| PEG-20 methyl glucosium sesquistearate | g 3.09 |
| stearyl alcohol + Steareth-20 ® + Steareth-10 ® | g 2.91 |
| isononylisononanoate | g 9.92 |
| hydrogenated lanoline | g 2.00 |
| C12-15 alkyl benzoate | g 3.08 |
| cyclomethicone | g 3.00 |
| methyl p-hydroxybenzoate | g 0.15 |
| propyl p-hydroxybenzoate | g 0.15 |
| water as it suffices to | g 100 |

TABLE I

Effect of the invention fucane sulphates having low molecular weight on the duration of the growing phase (anagen) of cultures of piliferous follicles isolated from human scalp.

| doses of depolymerized fucane sulphate μg/ml | % of growing piliferous follicles between the 3rd and the 28th day from the beginning of the experiment with respect to the third day (% growing follicles = 100) using the VO268.B (Ex. 5) preparation. In the first line below the days in which the observations have been effected are reported. | | | | | | | |
|---|---|---|---|---|---|---|---|---|
| | 3 | 7 | 10 | 14 | 17 | 21 | 24 | 28 |
| 80 | 100 | 98 | 94 | 86 | 71 | 59 | 37 | 18 |
| 0 | 100 | 95 | 82 | 67 | 40 | 25 | 5 | 0 |

TABLE II

Effect of the fucane sulphate having low molecular weight obtained by depolymerization in acid ambient (Ex. 8) on the duration of the growing phase of piliferous follicle cultures isolated from human scalp.

| doses of depolymerized fucane sulphate | % of growing piliferous follicles between the 3rd and the 28th day from the beginning of the experiment with respect to the third day (% growing follicles = 100) using the VO268.B (Ex. 5) preparation. In the first line below the days in which the observations have been effected are reported. | | | | | | | |
|---|---|---|---|---|---|---|---|---|
| µg/ml | 3 | 7 | 10 | 14 | 17 | 21 | 24 | 28 |
| 80 | 100 | 96 | 85 | 72 | 39 | 26 | 10 | 5 |
| 0 | 100 | 94 | 80 | 65 | 35 | 18 | 6 | 0 |

TABLE III

Effect of different preparations of the invention fucane sulphates having low molecular weight on the percentage of growing piliferous follicles on the seventeenth day of observation. The used concentration has been of 80 mcg/ml.

| Control | Ex. 4 | Ex. 6 | Ex. 7 | Ex. 10 |
|---|---|---|---|---|
| 35 | 70 | 65 | 75 | 58 |

What is claimed is:

1. A method of increasing the percentage of hair in the hair growth cycle of the scalp and for inhibiting Pytirosporum growth on the skin and scalp, said method comprising topically applying an effective amount of a depolymerized fucane sulphate to the skin or scalp requiring treatment, said fucane sulphate having the following parameters:

a molecular weight greater than 5,000 and up to 30,000 daltons;

5–16% sulfur;

25–60% fucose; and

2–25% uronic acids.

2. The method according to claim 1, wherein Pytirosporum is oval Pytirosporum.

3. The method according to claim 1, wherein the depolymerized fucane sulphate is obtained from *Fucus vesiculosus, Ascophyllum nodosum, Ecklonia kurome, Eisenia bicyclis, Laminaria digitata, Laminaria japonica, Padina pavonia, Pelvetia canaliculata, Sargassum linifolium*, and *Undaria pinnatifda*.

4. The method according to claim 1, wherein the depolymerized fucane sulphate has the following parameters:

a molecular weight greater than 5,000 and up to 14,000 daltons;

5–12% sulfur;

25–43% fucose; and

9–25% uronic acids.

5. The method according to claim 1, wherein the depolymerized fucane sulphate is added to a topical composition at a concentration of 0.01–20% w/v.

6. The method according to claim 5, wherein the topical form of said composition comprises lotions and shampoos and the concentration of the depolymerized fucane sulphate is present in the range of amounts of 0.01–1.0% w/v.

7. The method according to claim 5, wherein the topical form of said composition comprises creams and gels and the concentration of the depolymerized fucane sulphate is present in the range of amounts of 0.1–20% w/v.

* * * * *